United States Patent …

(12) United States Patent
Maschke

(10) Patent No.: US 7,197,112 B2
(45) Date of Patent: Mar. 27, 2007

(54) METHOD OF POSITIONING A MOBILE X-RAY DETECTOR UNIT OF AN X-RAY SYSTEM, X-RAY SYSTEM AND MOBILE X-RAY DETECTOR UNIT

(75) Inventor: Michael Maschke, Lonnerstadt (DE)

(73) Assignee: Siemens Aktiengesellschaft, Munich (DE)

( * ) Notice: Subject to any disclaimer, the term of this patent is extended or adjusted under 35 U.S.C. 154(b) by 76 days.

(21) Appl. No.: 10/948,416

(22) Filed: Sep. 23, 2004

(65) Prior Publication Data

US 2005/0063512 A1    Mar. 24, 2005

(30) Foreign Application Priority Data

Sep. 24, 2003 (DE) ............... 103 44 364

(51) Int. Cl.
*H05G 1/08* (2006.01)

(52) U.S. Cl. .................. 378/91; 378/116; 378/189
(58) Field of Classification Search ........ 378/114–116, 378/189, 91
See application file for complete search history.

(56) References Cited

U.S. PATENT DOCUMENTS

| | | | | |
|---|---|---|---|---|
| 3,947,689 A | * | 3/1976 | Wagner | ............. 378/151 |
| 4,027,156 A | * | 5/1977 | Robinet | ............. 378/117 |
| 5,877,501 A | * | 3/1999 | Ivan et al. | ............. 250/370.09 |
| 5,920,070 A | * | 7/1999 | Petrick et al. | ......... 250/370.09 |
| 6,091,982 A | | 7/2000 | Reinke et al. | |
| 6,302,580 B1 | * | 10/2001 | Dwyer et al. | ............. 378/197 |
| 2002/0150214 A1 | * | 10/2002 | Spahn | ............. 378/189 |
| 2003/0219100 A1 | * | 11/2003 | Okoda | ............. 378/102 |

FOREIGN PATENT DOCUMENTS

| | | |
|---|---|---|
| DE | 195 16 451 A1 | 11/1996 |
| DE | 101 18 745 C2 | 10/2002 |
| EP | 1 336 378 A1 | 8/2003 |
| JP | 11009579 * | 1/1999 |

* cited by examiner

*Primary Examiner*—Edward J. Glick
*Assistant Examiner*—John M. Corbett

(57) ABSTRACT

Method of positioning a mobile X-ray detector unit of an X-ray system, X-ray system and mobile X-ray detector unit.

method is described for positioning a mobile X-ray detector unit (25, 26) of an X-ray system (1). The X-ray system (1) deployed has X-ray radiation units (5, 6, 7) and at least one mobile X-ray detector unit (25, 26). The X-ray radiation units (5, 6, 7) thereby each have an active and a passive operating status. The X-ray radiation units (5, 6, 7) are each assigned a detector holder (8, 9, 10, 11, 12) to hold a mobile X-ray detector unit (25, 26). To generate X-ray recordings, X-ray radiation emitted by an active X-ray radiation unit (5, 6, 7) is detected by means of a mobile X-ray detector unit (25, 26), which is located in a detector holder (8, 9, 10, 11, 12) of said X-ray radiation unit (5, 6, 7). A mobile X-ray detector unit (25, 26) is positioned as a function of the operating status of the X-ray radiation units (5, 6, 7) such that a mobile X-ray detector unit (25, 26) is located in each of the detector holders (8, 9, 10, 11, 12) assigned to the active X-ray radiation units (5, 6, 7). A location unit is used to determine the location of a mobile X-ray detector unit automatically.

10 Claims, 1 Drawing Sheet

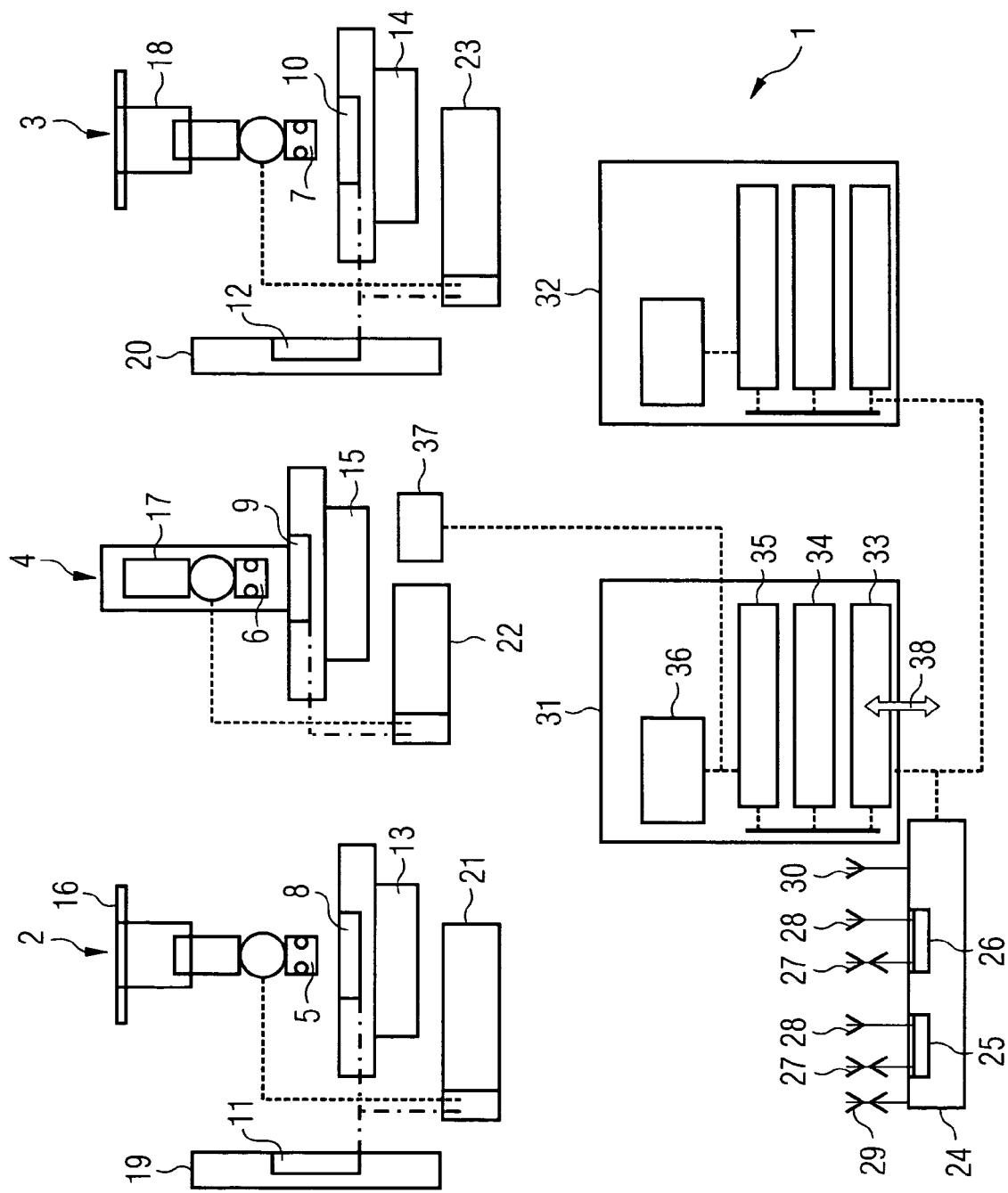

METHOD OF POSITIONING A MOBILE X-RAY DETECTOR UNIT OF AN X-RAY SYSTEM, X-RAY SYSTEM AND MOBILE X-RAY DETECTOR UNIT

CROSS REFERENCE TO RELATED APPLICATIONS

This application claims priority to the German application No. 10344364.9, filed Sep. 24, 2003 and which is incorporated by reference herein in its entirety.

FIELD OF INVENTION

The invention relates to a method for positioning a mobile X-ray detector unit of an X-ray system, a corresponding X-ray system—whereby the X-ray system comprises a plurality of X-ray radiation units and at least one mobile X-ray detector unit—and a corresponding mobile X-ray detector unit.

BACKGROUND OF INVENTION

The increasingly noteworthy technical development in the field of X-ray technology has recently resulted in the development, testing and supply of X-ray detector units, such as digital X-ray detector units based on semiconductors. The use of such X-ray detector units, particularly the integration of such X-ray detector units in a device gantry or an examination table has led to the creation of X-ray systems, which are technically superior to conventional X-ray systems, which use film cassettes or image intensifiers for recording purposes. The time and effort required for film development can therefore be eliminated by equipping X-ray systems with X-ray detector units. Also when using X-ray detector units the X-ray recordings are immediately available, the image quality of the X-ray recordings is better and the dose of X-ray radiation required is smaller. However the high production costs for such X-ray detector units have hitherto prevented their widespread use.

SUMMARY OF INVENTION

The U.S. Pat. No. 6,091,982 discloses a diagnostic unit with a mobile signal recorder and a stationary evaluation unit. A bi-directional communication connection is established between the signal recorder and the stationary evaluation unit by means of a suitable communication unit.

US 2002-0150214 A1 discloses an X-ray device with a transportable radiation receiver and a mobile controller. A wireless communication connection is thereby established between the transportable radiation receiver and the mobile controller.

The use of such transportable radiation receivers has the advantage that a radiation receiver can be used in a plurality of examination rooms and utilization of the radiation receiver can thereby be increased compared with a stationary radiation receiver. One disadvantage of the prior art however is that—in particular in systems with a plurality of mobile signal recorders or transportable radiation receivers and a plurality of examination rooms—the mobile signal recorders or transportable radiation receivers can frequently only be located with difficulty and as a result the diagnostic device or X-ray device as a whole can only be operated with inadequate efficiency.

It is therefore an object of the invention to specify a method for positioning a mobile X-ray detector unit of an X-ray system, a corresponding X-ray system and a mobile X-ray detector unit, which allow efficient deployment of a mobile X-ray detector unit.

This object is achieved by claims. There are also developments of the device Claims in the context of the invention, which correspond to the dependent method Claims.

With the inventive method a mobile X-ray detector unit to be positioned is deployed within an X-ray system which comprises X-ray radiation units and at least one mobile X-ray detector unit, whereby the number of X-ray radiation units is preferably greater than the number of X-ray detector units. The X-ray radiation units thereby each have an active and a passive operating status, whereby an X-ray radiation unit with active operating status emits X-ray radiation. Also the X-ray detector units are each assigned a detector holder to hold a mobile X-ray detector unit. To produce X-ray recordings, X-ray radiation emitted by an active X-ray radiation unit is detected by means of a mobile X-ray detector unit, which is disposed in a detector holder assigned to the active X-ray radiation unit. An X-ray radiation unit with passive operating status generally does not emit X-ray radiation, i.e. no X-ray recordings are made. "X-ray recording" here refers in particular to the image result of fluoroscopy method as well as the image result of an X-ray recording method or radiography method.

In order ultimately to enable efficient and therefore economical deployment of an expensive, in particular a digital and/or semiconductor-based mobile X-ray detector unit, a mobile X-ray detector unit is positioned as a function of the operating status of the X-ray radiation units such that there is a mobile X-ray detector unit located in each instance in the detector holder assigned to an active X-ray radiation unit. If the X-ray system has a plurality of mobile X-ray detector units, their positioning is coordinated such that there is a mobile X-ray detector unit located in each instance in all the detector holders assigned to an active X-ray radiation unit. The current location of a mobile X-ray detector unit is automatically detected by a location unit.

In particular the invention is therefore based on the idea of reducing the number of X-ray detector units required for an X-ray system with a plurality of X-ray radiation units by configuring the X-ray detector unit as mobile. It can then always be used in a flexible manner with the X-ray radiation unit, which has active operating status, in order to generate an X-ray recording in conjunction with the mobile detector unit located in the corresponding detector holder. To be able to coordinate the assignment of mobile X-ray detector units to X-ray radiation units efficiently, the current location of a mobile X-ray detector unit is determined automatically.

This means in particular that the mean daily operating time of an X-ray detector unit is longer compared with conventional systems with permanently integrated X-ray detector units. The X-ray detector unit in question is therefore be tter utilized. This means ultimately that the inventive X-ray system with a plurality of X-ray radiation units and at least one X-ray detector unit can be produced, installed and operated more economically.

The invention thereby utilizes the knowledge that the time for which an X-ray radiation unit has active status is short, compared with the time for which an X-ray radiation unit has passive status. This is also due to the fact that the preparation for a recording, such as for example the positioning of a patient in front of an X-ray radiation unit or the acquisition of patient data takes a great deal of time compared with the actual recording time, i.e. the period of active operating status of the X-ray radiation unit.

One further aspect of the invention is to retrofit X-ray radiation units of already existing conventional X-ray systems—i.e. X-ray systems, which are provided for deployment with X-ray cassettes or image intensifiers—for the deployment of modern X-ray detector units with a detector holder for mobile X-ray detector units in each instance. For this purpose a detector holder can in particular form part of a standard retrofit module. This means that the above-mentioned flexible deployment of a mobile X-ray detector unit can also be achieved subsequently for existing X-ray systems without incurring major additional costs.

The invention is also achieved by an X-ray system with a plurality of X-ray radiation units, each of which is assigned a detector holder for holding a mobile X-ray detector unit, and with at least one mobile X-ray detector unit, whereby the detector holders and a mobile X-ray detector unit are configured such that the mobile X-ray detector unit can be connected in an optionally interchangeable manner to the detector holders. A mobile X-ray detector unit thereby has a location unit to determine the location of the mobile X-ray detector unit automatically.

So that the mobile X-ray detector unit can be connected in an optionally interchangeable manner to the detector holders, the detector holders and the mobile X-ray detector unit or the mobile X-ray detector units have mutually corresponding mechanical and IT interface devices. This means that the active X-ray radiation units can be supplied in a flexible manner with mobile X-ray detector units.

The X-ray system preferably has X-ray sub-systems, each of which has at l east one X-ray radiation unit and at least one detector holder assigned to the X-ray radiation unit for a mobile X-ray detector unit. The X-ray sub-systems can thereby be configured as fluoroscopy systems and/or as radiography systems and correspondingly generate (quasi) continuous and/or discrete X-ray recordings. For this purpose the X-ray radiation units in particular are configured correspondingly as X-ray fluoroscopy radiation units and/or as radiography radiation units or as X-ray recording units. A mobile X-ray detector unit can be configured to operate in conjunction with an X-ray fluoroscopy radiation unit or a radiography radiation unit or X-ray recording unit. It is particularly preferable for the mobile X-ray detector unit to be configured such that it can operate in conjunction both with different X-ray fluoroscopy radiation units and with different X-ray recording units.

An X-ray radiation unit for mobile X-ray detector units can preferably also be assigned a plurality of detector holders, which are integrated for example in a table or wall gantry. Generally when producing an X-ray recording it is sufficient if a mobile X-ray detector unit is located in one of the detector holders of an active X-ray radiation unit; the remainder of the detector holders assigned to the active X-ray radiation unit can then remain empty.

The X-ray system preferably has a parking unit to hold a m obile X-ray detector unit that is not currently required or a plurality of X-ray detector units that are not currently required. Such a parking unit preferably serves as the center of the X-ray system, from which the mobile X-ray detector unit or mobile X-ray detector units are allocated as required to the active X-ray radiation units. This parking unit also preferably serv es as a supply and/or communication center. For this purpose the parking unit also has mechanical and IT interface devices, which correspond to interface devices of a mobile X-ray detector unit. These interface devices each comprise in particular at least one detector holder for a mobile X-ray detector unit or are each part of a detector holder for a mobile X-ray detector unit. The IT interface devices of a parking unit comprise in particular a link point for the e fficient transmission of recorded image data from the mobile X-ray detector unit to the parking unit. This is preferably a wireless interface, so that the data can be transmitted du ring transportation of the mobile X-ray detector unit from the X-ray radiation unit to the parking unit. Alternatively another link point can also be used, e.g. an electrical or o ptoelectronic link point.

The parking unit is preferably assigned one or a plurality of imaging systems, i.e. the parking unit is connected to one or a plurality of imaging systems or the parkin g unit comprises an imaging system or a plurality of imaging systems. An imaging system hereby preferably comprises an image data interface, an imaging system controller, an image processing unit and a display unit, e.g. a monitor or a display. The display unit preferably also serves, as described in more d etail below, to show the position of the mobile X-ray detector units. The components of the imaging system are in particular connected to each other by means of a data or system bus. The imaging system is preferably connected via the image data interface to the parking unit and/or a data and image network, so that image data can also be displayed on other display units, which are for example remote from the imaging system.

To supply a mobile X-ray detector unit with power, the mobile X-ray detector unit preferably has an accumulator unit. This accumulator unit can be charged with power via the above-mentioned interface device, when the mobile X-ray detector unit is located in a detector holder in the parking unit or an X-ray radiation unit. Additionally or alternatively a mobile X-ray detector unit has a power pack, which enables the accumulator to be charged or enables a temporary power supply at the place of deployment.

A mobile X-ray detector unit is also preferably equipped with a storage device in particular for patient data. Patient data thereby comprises in particular information describing the patient's X-ray recordings, e.g. digital image data, personal patient data, e.g. name and age, and/or X-ray recording specification data, which for example specifies the basic conditions for the X-ray recording, e.g. the part of the body to be examined or the recording perspective, in more detail.

This data can be written to the storage device and/or read from the storage device via a suitable interface when the mobile detector unit is held in a detector holder, which is assigned to an X-ray radiation unit, and/or when the mobile detector unit is held in a parking unit. Patient data is preferably written to the storage device of the mobile X-ray detector unit or read from a storage device of the mobile X-ray detector unit via a data and image network, which is connected to the parking unit, when the mobile X-ray detector unit is "parked" in the parking unit. Once the mobile X-ray detector unit is located in a detector holder, which is assigned to an X-ray radiation unit, patient data required for the X-ray recording is automatically read by the mobile X-ray detector unit and the recording is made according to the patient data. There is therefore no need to input patient data manually in the examination room.

It is particularly preferable for the mobile X-ray detector unit to be equipped with a transmitter and/or receiver unit for transmitting patient data and/ or image data. The mobile X-ray detector unit can thereby communicate via the transmitter and/or receiver unit, in particular via wireless access technologies such as DECT (Digital Enhanced Cordless Telecommunications), Bluetooth or W-LAN (Wireless Local Area Network), with the parking unit or a transmitter and/or receiver unit assigned to the parking unit, in order for example to be able to transmit image data during transportation of the mobile X-ray detector unit from the X-ray radiation unit to the parking unit.

According to a preferred embodiment, the link unit of a mobile X-ray detector unit, which is reserved for a specific patient, initiates the downloading of patient data relating to the specific patient via the transmitter and/or receiver unit from a central database to a detector holder assigned to an X-ray radiation unit.

In order to locate the mobile X-ray detector unit, the location unit comprises a GPS (Global Positioning System) receiver for example, to determine the current position coordinates of the mobile X-ray detector unit. These position coordinates can then be transmitted to the parking unit or a transmitter and/or receiver unit assigned to the parking unit and processed and/or displayed there. Alternatively the detector holders for mobile X-ray detector units are equipped with a sensor unit, which detects whether or not a mobile X-ray detector unit is currently located in the detector holder. The corresponding data is transmitted wirelessly or via a line-based communication network from the detector holders to the parking unit or a transmitter and/or receiver unit assigned to the parking unit and processed and/or displayed there. This means that the current location of the mobile detector units can be monitored from a central point, e.g. the parking unit.

BRIEF DESCRIPTION OF THE DRAWINGS

The invention is described in more detail below based on exemplary embodiments with reference to the accompanying FIGURE.

The single FIGURE shows a schematic illustration of an X-ray system with two radiography units and one fluoroscopy unit.

DETAILED DESCRIPTION OF INVENTION

The X-ray system 1 shown in the FIGURE comprises three X-ray subsystems. The X-ray subsystems are two radiography systems 2, 3 and one fluoroscopy system 4. It may however also have at least one portable, mobile X-ray unit as an X-ray subsystem.

The three X-ray subsystems 2, 3, 4 each have an X-ray radiation unit 5, 6, 7, which is supported in a movable manner by radiation gantries 16, 17, 18. The X-ray radiation unit 5, 6, 7 is configured in the radiography systems 2, 3 as a radiography radiation unit 5, 7 or X-ray recording unit and in the fluoroscopy system 4 as an X-ray fluoroscopy radiation unit 6.

The fluoroscopy system 4 is equipped in or on an examination table 15 with a detector holder 9 for a mobile X-ray detector unit. The radiography systems 2, 3 each have a first detector holder 8, 10 for a mobile X-ray detector unit at a table 13, 14 and a further detector holder 11, 12 for a mobile X-ray detector unit in or on a wall gantry 19, 20.

When using a mobile X-ray unit, which may for example be provided with a C-arm, an X-ray radiation unit can be arranged on one side of the C-arm and a detector holder on the other side.

The three X-ray subsystems 2, 3, 4 are each controlled by a system controller 21, 22, 23. The system controller 21, 22, 23 is thereby configured as a program-controlled computer device, which controls the major components of the relevant X-ray subsystem 2, 3, 4 and coordinates their interaction.

Assigned to it and controlled by the system controller 21, 22, 23 is an X-ray generator (not shown in the drawing) to generate the high voltage required for the X-ray radiation units 5, 6, 7. The system controller 21, 22, 23 also enables recording synchronization between the X-ray generator and the X-ray detector unit 25, 26.

The X-ray system 1 also has a parking unit 24, which also has detector holders for mobile X-ray detector units. Mobile X-ray detector units 25, 26 are currently located in the detector holders.

The mobile X-ray detector units 25, 26 each have a transmitter/receiver unit, of which only a transmitter/receiver antenna 27 is shown in the drawing. Data, in particular patient data or location information, can be transmitted from or to these transmitter/receiver units to or from a correspondingly configured transmitter/receiver unit in the parking unit 24. Only a transmitter/receiver antenna 29 of the transmitter/receiver unit is similarly shown in the drawing.

The mobile X-ray detector units 25, 26 are also equipped with GPS receivers, of which only the receiver antennae 28 are shown in the drawing. The position coordinates of the mobile X-ray detector units 25, 26 determined using the GPS receiver can then be transmitted via the transmitter/receiver units described above to the parking unit 24. Alternatively the position coordinates can also be transmitted in each instance via a further transmitter/receiver unit (not shown) provided specifically for this purpose in the relevant mobile X-ray detector unit 25, 26 to a transmitter/receiver unit communicating with this transmitter/receiver unit in the parking unit 24. The parking unit 24 also has a GPS receiver, of which only the receiver antenna 30 is shown in the drawing. The position coordinates received for the mobile X-ray detector units 25, 26 can then be aligned with the position coordinates determined for the parking unit 24, to determine the position of the relevant mobile X-ray detector unit 25, 26 in relation to the position of the parking unit 24.

The position of the mobile X-ray detector units 25, 26 thus determined can then be displayed on a display unit 36, e.g. a graphic display, at the parking unit 24 or a different central control center. This makes it possible to monitor the current location of the mobile X-ray detector units 25, 26 from the parking unit 24 or the above-mentioned central control center and to coordinate the allocation of mobile X-ray detector units 25, 26 to the X-ray radiation units such that there is always at least one mobile X-ray detector unit in the detector holders, which are assigned to a currently active X-ray radiation unit.

The above-mentioned display unit 36 is a major element of an imaging system 31, which can be connected via a suitable interface device, e.g. a data interface 33, and the parking unit 24, to mobile X-ray detector units 25, 26. As a result image data generated in the detector during an X-ray recording can be loaded from a storage device of a mobile X-ray detector unit 25, 26 into the imaging system 31, processed there by an image processing unit 35 and prepared for display on the display unit 36. As well as being displayed on the display unit 36 of the imaging system, image data can also be displayed by a further display unit 37, which is remote from the imaging system 31, for example in an examination room, subject to control by the imaging system 31.

The major components of the imaging system 31 and therefore the method implemented by the imaging system are controlled by an imaging system controller 34, which may be a program-controlled computer unit.

The imaging system 31 also has a further data and image interface 38 with a data and image network, to transmit patient data, in particular image data, from and/or to the imaging system 31 or the parking unit 24. For example the imaging system 31 or the parking unit 24 is connected via the data and image interface 38 to a further imaging system 32, the structure and mode of operation of which can be configured according to the structure and mode of operation of the imaging system 31 described above. The data and image inteiface 38 thereby preferably operates according to a general standard, e.g. the DICOM (Digital Imaging and Communication) standard. Such a second imaging system 32 can accelerate image processing, as two mobile detectors can be read in pa rallel. However this is not absolutely necessary, as the image data of the individual mobile detectors can also be taken from an imaging system and processed sequentially.

According to one advantageous embodiment not shown in the FIGURE, the parking unit 24 is connected via an automatic transport system, e.g. a rail system, configured for the transportation of a mobile X-ray detector unit 25, 26, to the X-ray subsystems 2, 3, 4. When a patient is positioned appropriately by hospital personnel in the radiography sy stem 2 between the holder sub-unit 8 and the X-ray radiation unit 5, the transmission of an X-ray detector request message from the radiography system 2 to the parking unit 24 i s initiated manually or automatically. A mobile X-ray detector unit 25 is then transported automatically via the transport system to the radiography system 2 and inserted into the holder sub-unit 8. As soon as a detector device detects the presence of a mobile X-ray detector unit 25 in the detector holder 8, firstly a release signal is sent to the system controller 21 to initiate activation of the X-ray radiation unit 5 and secondly location information specifying the detector holder or examination room, in which the mobile X-ray detector unit 25 is located, is sent to the parking unit 24.

If, after the recording, the X-ray radiation unit 5 is switched back to passive operating mode, the mobile X-ray detector unit 25 is automatically transported via the transport system to the parking unit 24 to wait there for the next X-ray detector request message. During this waiting period and/or during the transport period the image data detected during recording is transmitted to the imaging system 31. Depending on the configuration, the X-ray detector request message, patient data and/or image data can be transmitted wirelessly or in a line-based manner between the mobile X-ray detector unit 25, the parking unit 24, the imaging system 31 and/or the data and image network.

It should be pointed out specifically again here that the X-ray system shown in the FIGURE is only an exemplary embodiment of the invention. For example all or some of the transmitter and/or receiver units can be wireless or line-based. Wireless and/or line-based data transmission can thereby be effected according to transmission standards known per se, e.g. Bluetooth or WLAN, or according to transmission methods developed specifically for this purpose. The X-ray system can have any number of radiography systems or any number of fluoroscopy systems but does not have to have a radiography sy stem or a fluoroscopy system. The parking unit can be central or distributed, for example with individual parking units assigned to the X-ray radiation units. The imaging system can be both an integral part of the parking unit or an X-ray subsystem.

The invention claimed is:

1. A method of allocating a mobile X-ray detector alternately to a plurality of X-ray radiation units, each X-ray radiation unit comprising an active or passive operating status and each X-ray radiation unit comprising a detector holder for releasably holding the mobile X-ray detector unit, the method comprising:
assigning the X-ray radiation unit as a function of the operating statuses of the X-ray radiation units such that the mobile X-ray detector unit is located in the detector holder of an active X-ray radiation unit;
inserting the mobile X-ray detector in the detector holder of said active X-ray radiation unit;
determining a location of the mobile X-ray detector unit via a localization unit in the mobile X-ray detector or in the detector holder of said active X-ray radiation units; and
transmitting the location of the mobile X-ray detector to a parking unit comprising an additional detector holder.

2. The method of claim 1, wherein the localization unit comprises a first global positioning system receiver in the mobile X-ray detector.

3. The method of claim 2, wherein the parking unit further comprises a second global positioning system receiver, and the method further comprises comparing position coordinates of the first and second global positioning system receivers to determine a location of the mobile X-ray detector relative to the parking unit.

4. The method according to claim 1, further comprising:
emitting X-ray radiation by said active X-ray radiation unit;
generating X-ray images by detecting the X-ray radiation using the mobile detector unit and transmitting image data from the mobile X-ray detector unit to an imaging system via a wireless data communications receiver in the parking unit.

5. The method according to claim 4, further comprising storing the mobile X-ray detector in the parking unit between assignments.

6. An X-ray system, comprising:
a plurality of X-ray radiation units, each comprising a detector holder and an alternately active or passive operating status;
an imaging system;
at least one mobile X-ray detector unit alternately connectable to each of the detector holders and assigned to one of the X-ray radiation units as a function of the operating statuses of the X-ray radiation units, such that the mobile X-ray detector unit is located in the detector holder of an X-ray radiation unit in active operating status;
a localization unit in said at least one mobile X-ray detector unit configured to determine a current location of the mobile X-ray detector unit; and
a data communications link configured to transmit data from said at least one mobile X-ray detector unit to the imaging system, including imaging data and current location data.

7. The X-ray system according to claim 6, wherein the localization unit comprises a first global positioning system receiver in the mobile X-ray detector.

8. The X-ray system according to claim 7, wherein the localization unit further comprises a second global positioning system receiver in a parking unit electronically connected to the imaging system, and wherein a current location of the mobile X-ray detector relative to the parking unit is determined by comparing position coordinates of the first and second global positioning system receivers.

9. A mobile X-ray detector unit, comprising:
a mechanical interface configured to releasably connect the mobile X-ray detector alternately to a each of a plurality of detector holders assigned to a plurality of X-ray radiation units and alternately to a parking unit;
a data interface configured to establish a data communication connection between the mobile X-ray detector and the parking unit; and
a localization unit in the mobile X-ray detector configured to determine a current location of the mobile X-ray detector relative to the parking unit.

10. The mobile X-ray detector unit of claim 9, wherein the localization unit is a global positioning system receiver.

* * * * *